US006884912B1

(12) United States Patent
Bossoutrot et al.

(10) Patent No.: US 6,884,912 B1
(45) Date of Patent: Apr. 26, 2005

(54) AMINOGUANIDINE BICARBONATE WITH PARTICULAR PROPERTIES AND METHOD FOR MAKING SAME

(75) Inventors: Jean-Michel Bossoutrot, Chaponost (FR); Paul Bourdauducq, Chaponost (FR)

(73) Assignee: Atofina, Puteaux (FR)

( * ) Notice: Subject to any disclaimer, the term of this patent is extended or adjusted under 35 U.S.C. 154(b) by 199 days.

(21) Appl. No.: 10/031,113

(22) PCT Filed: Jun. 8, 2000

(86) PCT No.: PCT/FR00/01579

§ 371 (c)(1),
(2), (4) Date: Apr. 29, 2002

(87) PCT Pub. No.: WO01/05752

PCT Pub. Date: Jan. 25, 2001

(30) Foreign Application Priority Data

Jul. 16, 1999 (FR) ............................. 99 09257

(51) Int. Cl.[7] .............................................. C07C 277/02
(52) U.S. Cl. ...................................... 564/230; 252/6
(58) Field of Search ................................ 564/230, 232; 558/260, 262; 548/263.8, 263.2

(56) References Cited

FOREIGN PATENT DOCUMENTS

| DE | 249 009 A | 8/1987 |
|---|---|---|
| SU | 981 314 A | 12/1982 |

*Primary Examiner*—Karl J. Puttlitz

(57) ABSTRACT

The invention concerns a method for making aminoguanidine bicarbonate from an aqueous solution of cyanamide and an aqueous solution of hydrazine in the presence of $CO_2$. The invention is characterised in that it consists in proceeding with an amount of cyamide slightly higher than the stoichiometric quantity. The invention also concerns quasi-spherical agglomerates of aminoguanidine bicarbonate crystals.

13 Claims, 3 Drawing Sheets

AMINOGUANIDINE BICARBONATE WITH PARTICULAR PROPERTIES AND METHOD FOR MAKING SAME

The present invention relates to a process for manufacturing aminoguanidine bicarbonate. The invention also relates to an aminoguanidine bicarbonate with particular properties.

BACKGROUND OF THE INVENTION

The manufacture of aminoguanidine bicarbonate (AGB) by reacting an aqueous solution of cyanamide with hydrazine followed by an addition of $CO_2$ is known. Since the placing in contact of cyanamide with hydrazine in alkaline medium also leads to the dimerization of the cyanamide, it is necessary to use a large excess of cyanamide to achieve a suitable yield of aminoguanidine bicarbonate.

Thus, patent DD 689 191 teaches working with a 100% excess of cyanamide (i.e. cyanamide/hydrazine molar ratio= 2/1) to obtain a yield (relative to the hydrazine used) of 80% of AGB, after reaction for 60 hours. An AGB yield of about 90% may be achieved after reaction for 27 hours when concentrated solutions of cyanamide and hydrazine are used with a 100% excess of cyanamide (DD 730 331).

Since cyanamide is a very expensive product, attempts to reduce this excess have been the subject of much research.

Specifically, patent SU 981 314 discloses a cyanamide/hydrazine molar ratio of between 1.25 and 1.8. It is mentioned that an AGB yield (relative to the hydrazine) of 95% is obtained with a cyanamide/hydrazine molar ratio of 1.8. It also teaches that the yields fall to 90% and 85% for molar ratios of 1.5 and 1.25, respectively.

The same trend has been observed by other authors. Thus, a fall of about 12 points in the yield was recorded when the cyanamide/hydrazine molar ratio went from 1.2 to 1 (DD 249 009).

The combined literature in this field encourages a person skilled in the art to work with an excess of cyanamide to obtain a yield of aminoguanidine bicarbonate.

BRIEF SUMMARY OF THE INVENTION

The Applicant Company has developed a process for manufacturing aminoguanidine bicarbonate from cyanamide and hydrazine and has observed, surprisingly, by working with a slight deficit of cyanamide relative to the stoichiometric amount, yields of AGB that are as high as, or even higher than, those achieved with processes using a large excess of cyanamide.

According to the present invention, the process consists in reacting an aqueous solution of cyanamide with an aqueous solution of hydrazine hydrate in the presence of $CO_2$, characterized in that the process is performed with a slight deficit of cyanamide relative to the stoichiometry.

The cyanamide/hydrazine molar ratio used is preferably between 0.80 and 0.99 and advantageously between 0.85 and 0.95.

The pH of the reaction medium is generally between 6.5 and 8, preferably between 7 and 7.3. The pH may be adjusted by any suitable means and especially using $C_{-2}$.

The concentration of the aqueous solutions may vary within a wide range. It is usually preferred to use an aqueous cyanamide solution with a concentration of between 15% and 50% by weight. The hydrazine concentration in the aqueous solution is advantageously between 15% and 64% by weight.

The temperature of the reaction medium is generally between 35° C. and 70° C. A temperature of between 40° C. and 50° C. gives an aminoguanidine bicarbonate whose structure and specific properties are commercially very advantageous.

BRIEF DESCRIPTION OF THE FIGURES

Photograph 1 is a scanning electron microscopy photograph of the crystals obtained by the method described in Example 1 of the present specification.

Photograph 2 is a scanning electron microscopy photograph of the crystals obtained by the method described in Example 2 of the present specification.

Figure 1:
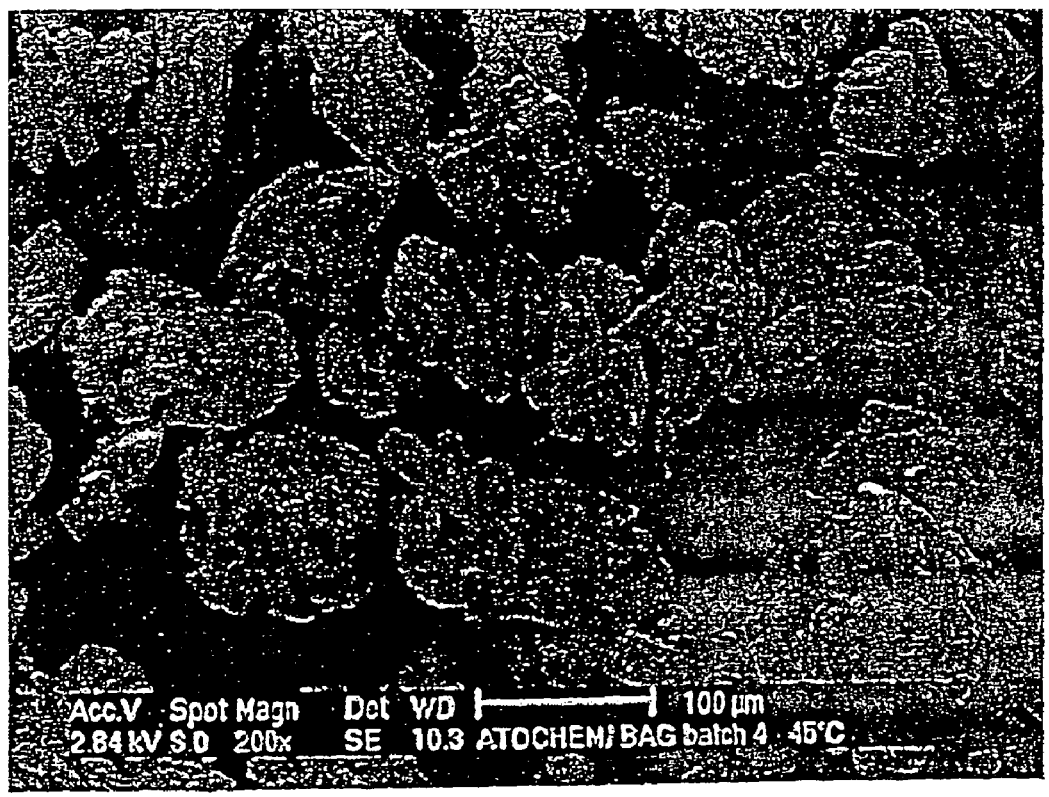
Figure 2:
Figure 3:
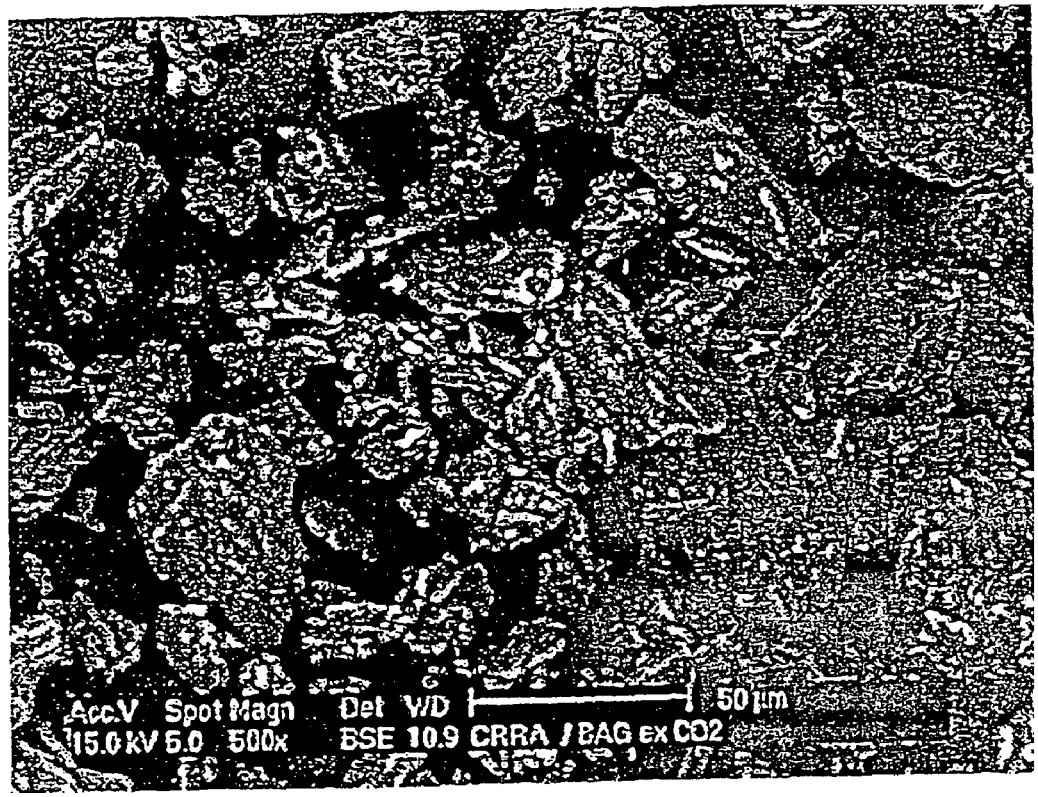

Photograph 3 is a scanning electron microscopy photograph of the crystals obtained by the method described in Example 5 of the present specification.

DETAILED DESCRIPTION OF THE PREFERRED EMBODIMENTS

One embodiment consists in adjusting, using $CO_2$ (carbon dioxide), the pH of the hydrazine hydrate solution to the desired value and then in introducing an aqueous solution of cyanamide once the temperature of the hydrazine solution has been raised to about a few degrees below the temperature chosen for the reaction.

The pH of the reaction medium is maintained using $CO_2$ at the desired value during the introduction, or addition, of the cyanamide solution and throughout the reaction.

Another embodiment consists in simultaneously adding an aqueous hydrazine hydrate solution and carbon dioxide to an aqueous cyanamide solution initially maintained a few degrees below the temperature chosen for the reaction.

Irrespective of the embodiment, the total reaction time is generally between 6 and 15 hours and preferably between 7 and 10 hours. The duration of the addition of cyanamide or of hydrazine hydrate is generally between 1 and 3 hours and preferably in the region of 2 hours.

After the reaction, the reaction medium is cooled to room temperature and the aminoguanidine bicarbonate thus obtained is spin-filtered or filtered and optionally dried.

With the process according to the invention, yields of greater than 90% and preferably greater than 95% are obtained with a purity of greater than 99%, or even greater than 99.5%.

A subject of the present invention is also an aminoguanidine bicarbonate with a particular structure and particular specific properties. It is characterized by a virtually spherical crystal aggregate with a mean diameter of between 80 and 500 µm. The aggregate preferably has a mean diameter of between 100 and 250 µm, the mean diameter being determined by laser granulometry.

The aminoguanidine bicarbonate according to the invention also has the advantage of being easy to separate out from the reaction medium by any known means, for example by filtering or spin-filtering and drying, thus being distinguished from platelet crystals.

EXAMPLES

Example 1

110.9 g of hydrazine hydrate with a purity of 99.2% (2.2 mol) and 300 g of demineralized water are placed in a one liter reactor at room temperature. The pH of the aqueous solution is in the region of 11. Carbon dioxide is then bubbled into the aqueous solution for about 1 hour, which represents 58 g or 1.3 mol f $CO_2$, until a pH in the region of 7 is obtained, while maintaining the temperature of the solution at about 40° C.

171.4 g of an aqueous 49% cyanamide solution (2 mol) are then added over about 2 hours, while continuing the addition of $CO_2$ so as to maintain the pH of the reaction medium in the region of 7. During the addition, the temperature of the medium is raised to 45° C. and the medium is maintained at this temperature for 8 hours with adjustment of the pH to a value in the region of 7 by small additions of $CO_2$.

The total amount of $CO_2$ added is 104 g, i.e. 2.36 mol.

At the end of the reaction, the reaction medium is allowed to cool to room temperature and the AGB crystals are then filtered off and washed with 250 ml of water and finally dried under vacuum at a temperature o-f between 35° C. and 40° C.

After drying, 260 g of crystals with a purity of 99.7%, determined by assaying with perchloric acid, are obtained. The crude yield relative to the cyanamide is 95.6%.

The crystals obtained are in the form of virtually spherical aggregates (photograph No. 1 by scanning electron microscopy).

Example 2

The process is performed as described in Example 1, except that the aqueous hydrazine hydrate solution is maintained at 55° C. instead of 40° C. and that, during the addition of the cyanamide, the reaction medium is brought to 65° C. and is maintained at this temperature for 4 hours.

After drying, 261.1 g of crystals in the form of platelets (photograph No. 2) are obtained with a purity of 99.6%. The crude yield relative to the cyanamide is 96%.

Example 3

Example 1 is extrapolated to the industrial scale, using a 15 m³ reactor.

After spin-filtering for 20 minutes, the aggregates contain a moisture content of only 7%. At the end of the spin-filtering, the aggregates are virtually spherical of the type in Example 1, with a narrow particle size distribution free of fine particles, of less than 40 μm in diameter.

Example 4

Example 2 is repeated on the industrial scale, using a 15 m³ reactor.

After spin-filtering for 3 hours, the platelets contain a moisture content of 20% and, at the end of the spin-filtering, the platelets have a mean diameter of 70 μm with a very broad particle size distribution with 20% of the population of particles having a diameter of less than 20 μm.

Example 5

The procedure described in Example 1 is repeated, except that the duration of addition of the cyanamide is 5 hours instead of 2 hours and the duration of the reaction after the addition is reduced from 8 to 5 hours.

The yield and also the purity of the AGB crystals obtained are similar to those of Example 1. However, the crystals are rather in the form of platelets (photograph No. 3) and the spin-filtering time is longer.

Example 6

171.4 g of an aqueous 49% cyanamide solution (2 mol) and 300 g of water are placed in a one liter reactor at room temperature. The pH of the resulting solution is in the region of 5. The solution is then brought to 40° C.; after which 110.9 g of 99.2% hydrazine hydrate (2.2 mol) and 75 g (1.7 mol) of $CO_2$, to maintain the pH at about 7, are simultaneously added over 2 hours. The reaction medium is then maintained at 45° C. for 8 hours with a small addition of $CO_2$ to adjust the pH to about 7. The total amount of $CO_2$ added is 94.5 g (2.15 mol).

The reaction medium is then allowed to-cool to room temperature and the AGB is filtered off and washed with 250 ml of water. Finally, it is dried under vacuum at a temperature of between 35° C. and 40° C.

After drying, 259 g of AGB aggregates similar to those of Example 1, with a purity of 99.6%, are obtained.

The crude yield of aminoguanidine bicarbonate is 95.2% relative to the cyanamide.

What is claimed is:

1. A process for manufacturing aminoguanidine bicarbonate, comprising combining an aqueous solution of cyanamide and an aqueous solution of hydrazine hydrate to form a reaction medium in the presence of $CO_2$, wherein the molar ratio of the cyanamide to the hydrazine used in the process is smaller than 1.

2. The process as claimed in claim 1, wherein the cyanamide/hydrazine molar ratio used is between about 0.8 and about 0.99.

3. The process as claimed in claim 2, wherein the cyanamide/hydrazine molar ratio is between about 0.85 to about 0.95.

4. The process as claimed in claim 1, wherein the pH of the reaction medium is between about 6.5 and about 8.

5. The process as claimed in claim 4, wherein the pH of the reaction medium is between about 7 and about 7.3.

6. The process as claimed in claim 1, wherein the temperature of the reaction medium is between about 35° C. and about 70° C.

7. The process as claimed in claim 6, wherein the temperature of the reaction medium is between about 40° C. and about 50° C.

8. The process as claimed in claim 1, wherein the pH of the hydrazine hydrate solution is adjusted using $CO_2$, and the aqueous cyanamide solution is then introduced.

9. The process as claimed in claim 1, wherein the hydrazine hydrate solution and $CO_2$ are simultaneously added to the cyanamide solution.

10. The process as claimed in claim 1, wherein the cyanamide solution or of the hydrazine hydrate solution is kept being added to the reaction medium for between about 1 and about 3 hours.

11. A process for manufacturing aminoguanidine bicarbonate, comprising combining an aqueous solution of cyanamide and an aqueous solution of hydrazine hydrate to form a reaction medium in the presence of $CO_2$, wherein the molar ratio of the cyanamide to the hydrazine used in the process is between about 0.8 and about 0.99, wherein the pH of the reaction medium is between about 6.5 and about 8, and wherein the temperature of the reaction medium is between about 35° C. and about 70° C.

12. A virtually spherical aggregate of amino guanidine bicarbonate crystals with a mean diameter of between about 80 and about 500 μm.

13. The virtually spherical aggregate of amino guanidine bicarbonate crystals of claim 12, wherein the mean diameter is between about 100 and about 250 μm.

* * * * *